US010886021B2

(12) United States Patent
Rudser

(10) Patent No.: US 10,886,021 B2
(45) Date of Patent: Jan. 5, 2021

(54) INTERMEDIATE POWER SUPPLY WITH SENSING AND COMMUNICATION SYSTEM

(71) Applicant: HeartWare, Inc., Miami Lakes, FL (US)

(72) Inventor: John Rudser, Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 594 days.

(21) Appl. No.: 15/812,566

(22) Filed: Nov. 14, 2017

(65) Prior Publication Data

US 2019/0147140 A1 May 16, 2019

(51) Int. Cl.
*A61M 1/12* (2006.01)
*G16H 40/40* (2018.01)
(Continued)

(52) U.S. Cl.
CPC .......... *G16H 40/40* (2018.01); *A61M 1/1086* (2013.01); *A61M 1/122* (2014.02); *A61M 1/127* (2013.01); *G06F 19/3418* (2013.01); *A61M 2205/18* (2013.01); *A61M 2205/3317* (2013.01); *A61M 2205/3368* (2013.01); *A61M 2205/3523* (2013.01); *A61M 2205/50* (2013.01); *A61M 2205/502* (2013.01); *A61M 2205/52* (2013.01); *A61M 2205/581* (2013.01); *A61M 2205/583* (2013.01); *A61M 2205/80* (2013.01); *A61M 2205/8206* (2013.01); *H02M 7/02* (2013.01)

(58) Field of Classification Search
None
See application file for complete search history.

(56) References Cited

U.S. PATENT DOCUMENTS 10,127,356 B2 * 11/2018 Colburn ............ G06Q 10/0639
10,321,907 B2 * 6/2019 Shelton, IV ...... H01M 10/6235
(Continued)

FOREIGN PATENT DOCUMENTS

WO 2007053881 A1 5/2007

OTHER PUBLICATIONS

International Search Report and Written Opinion dated Jan. 21, 2019, for corresponding International Application No. PCT/US2018/054512; International Filing Date: Oct. 5, 2018 consisting of 12-pages.

*Primary Examiner* — K. Wong
(74) *Attorney, Agent, or Firm* — Christopher & Weisberg, P.A.

(57) ABSTRACT

A method, device, and system for collecting data from one or more sensors in an intermediate power supply (IPS) between a main power source and a control system of a medical system, and transmitting data to the control system. Data received by the control system may include information about the operating parameters of the IPS and may be displayed or communicated to the user, allowing the user to adjust operation of the IPS and/or the medical system in response thereto. In one embodiment, a medical system comprises a clinical device, a control system in electrical communication with the clinical device, and an IPS in electrical communication with the control system, the IPS being configured to be in electrical communication with a main power source. The IPS includes a sensing and communication system having at least one sensor and processing circuitry in communication with the at least one sensor.

19 Claims, 3 Drawing Sheets

(51) Int. Cl.
  *G06F 19/00* (2018.01)
  *A61M 1/10* (2006.01)
  *H02M 7/02* (2006.01)

(56) References Cited

U.S. PATENT DOCUMENTS

| | | |
|---|---|---|
| 10,381,849 B2 * | 8/2019 | Wing .................... H02J 7/0063 |
| 10,425,894 B2 * | 9/2019 | Howell .................. G16H 40/63 |
| 2010/0241223 A1 | 9/2010 | Lee et al. |
| 2011/0072970 A1 | 3/2011 | Slobodzian et al. |
| 2015/0290373 A1 | 10/2015 | Rudser et al. |
| 2015/0290374 A1 | 10/2015 | Bourque et al. |
| 2017/0246366 A1 | 8/2017 | Rudser |

* cited by examiner

INTERMEDIATE POWER SUPPLY WITH SENSING AND COMMUNICATION SYSTEM

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a method, device, and system for collecting data from one or more sensors in an intermediate power supply between a main power source and a control system of a medical system, and transmitting data to the control system.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as a ventricular assist device (VAD).

A VAD is a device which is used to assist the heart of a mammalian subject, such as a human patient. A typical VAD includes a pump that is implanted in the body of the subject. The pump typically has an inlet connected to a source of blood to be circulated, and an outlet connected to an artery. Most typically, the inlet of the pump is connected to the interior of the left ventricle and the outlet of the pump is connected to the aorta, so that the pump operates in parallel with the left ventricle to impel blood into the aorta. The pump may be a miniature rotary impeller pump having an impeller disposed in a pump housing and driven in rotation by one or more small electric motors which may be closely integrated with the pump. The motor in turn typically is connected via percutaneous, biocompatible driveline to a power source, such as a battery or central power supply unit. The VAD typically includes a control system which controls operation of the power source so as to drive the impeller at a set rotational speed and thus provide constant pumping action.

In some currently known systems, the VAD receives power from one or more rechargeable batteries and/or from an AC/DC power supply for connecting to a source of mains electricity (for example, electricity provided from a wall outlet). The control system also receives power from the AC/DC power supply. The AC/DC power supply may include a simple display or indicator (such as an LED) to indicate charge status and/or alert condition. For example, the LED may glow green if power is flowing normally through the AC/DC power supply from the main power source to the control system. Alternatively, the LED is unlit if the AC/DC power supply is not properly connected to the main power source, or the LED may glow red if the AC/DC power supply is failing to supply power to the control system. However, this indicator does not provide much information to the user about what may be causing an improper connection between the source of power and the load. This may include an interruption in the flow of electricity between, the AC/DC power supply and the main power source and/or information about the status of electricity flow from the main power source, through the AC/DC power supply to the control system.

SUMMARY

The present invention relates to a method, device, and system for collecting data from one or more sensors in an intermediate power supply between a main power source and a control system of a medical system, and transmitting data to the control system, patient, caregiver, clinic, or the like. Data received by the control system may include information about the operating parameters of the intermediate power supply and may be displayed or communicated to the user, allowing the user to take action, which may include adjusting operation of the intermediate power supply and/or the medical system in response thereto.

In one embodiment, a medical system comprises: a clinical device; a control system in electrical communication with the clinical device; and an intermediate power supply in electrical communication with the control system, the intermediate power supply being configured to be in electrical communication with a main power source, the intermediate power supply including a sensing and communication system having: at least one sensor; and processing circuitry in communication with the at least one sensor.

In one aspect of the embodiment, the control system includes processing circuitry, the processing circuitry of the intermediate power supply being configured to transmit data to and receive data from the processing circuitry of the control system.

In one aspect of the embodiment, the at least one sensor includes at least one of: a piezoelectric sensor; a temperature sensor; a humidity sensor; an accelerometer; an impedance sensor; a voltage sensor; a fluid ingress sensor; a current sensor; and a time sensor.

In one aspect of the embodiment, the medical system further comprises a user input display in electrical communication with the control system.

In one aspect of the embodiment, the user input display is configured to receive data from the control system and to display information to a user, the information being based on the received data.

In one aspect of the embodiment, the user input display is further configured to receive audible information from a user and audibly communicate information to the user in the user's native language.

In one aspect of the embodiment, the information includes at least one of: a line voltage of electricity received by the intermediate power supply from the main power source; an output voltage of electricity transmitted from the intermediate power supply to the control system; a line current of electricity received by the intermediate power supply from the main power source; an output current of electricity transmitted from the intermediate power supply to the control system; an operating temperature of the intermediate power supply; and a total usage of the medical system, the total usage being expressed in at least one of voltage, current, and time.

In one aspect of the embodiment, the processing circuitry of the intermediate power supply is configured to: record at least one operating parameter of the intermediate power supply; compare the at least one operating parameter to a threshold value; and generate alert instructions based on the comparison.

In one aspect of the embodiment, the control system is configured to receive the alert instructions from the intermediate power supply, to log alert instructions, and to generate at least one alert based on the alert instructions, the at least one alert being at least one of: an audible alert; and a visual alert.

In one aspect of the embodiment, the user input display is configured to display the visual alert.

In one aspect of the embodiment, the processing circuitry of the intermediate power supply is further configured to automatically electrically disconnect from the control system based on the alert instructions.

In one aspect of the embodiment, the sensing and communication system further has a wireless communication unit configured to wirelessly transmit and receive data from the control system.

In one aspect of the embodiment, the sensing and communication system further has a communication bus configured to transmit and receive data from the control system.

In one aspect of the embodiment, the clinical device is a ventricular assist device.

In one embodiment, an intermediate power is configured to be connected between a main power source and a control system of a medical system. In this embodiment, the intermediate power supply comprises: at least one sensor, the at least one sensor being configured to record data relating to at least one operating parameter of the intermediate power supply; and processing circuitry in communication with the at least one sensor, the processing circuitry being configured to receive the data from the at least one sensor and to compare the data to at least one threshold value.

In one aspect of the embodiment, the intermediate power supply is configured to receive alternating current electricity from a main power source and to transmit direct current electricity.

In one aspect of the embodiment, the intermediate power supply is configured to be in electrical communication with, and transmit direct current electricity to, a control system of a medical system.

In one aspect of the embodiment, the intermediate power supply is configured to automatically electrically disconnect from the control system based on the comparison.

In one aspect of the embodiment, the intermediate power supply is configured to generate alert instructions based on the comparison.

In one aspect of the embodiment, the at least one sensor includes at least one of: a piezoelectric sensor; a temperature sensor; a humidity sensor; an accelerometer; an impedance sensor; a voltage sensor; a fluid ingress sensor; a current sensor; and a time sensor.

In one embodiment, an intermediate power supply for use with a medical system is configured to receive alternating current electricity from a main power source and to transmit direct current electricity to a control system of the medical system. In this embodiment, the intermediate power supply comprises: at least one sensor; and processing circuitry in communication with the at least one sensor, the processing circuitry including a memory and a processor, the memory in communication with the processor, the memory having instructions that, when executed by the processor, configure the processor to: receive measurement data from the at least one sensor; compare the measurement data to a threshold value to generate at least one of operations data and alert instructions; and transmit the at least one of operations data and alert instructions to a control system of a medical system.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
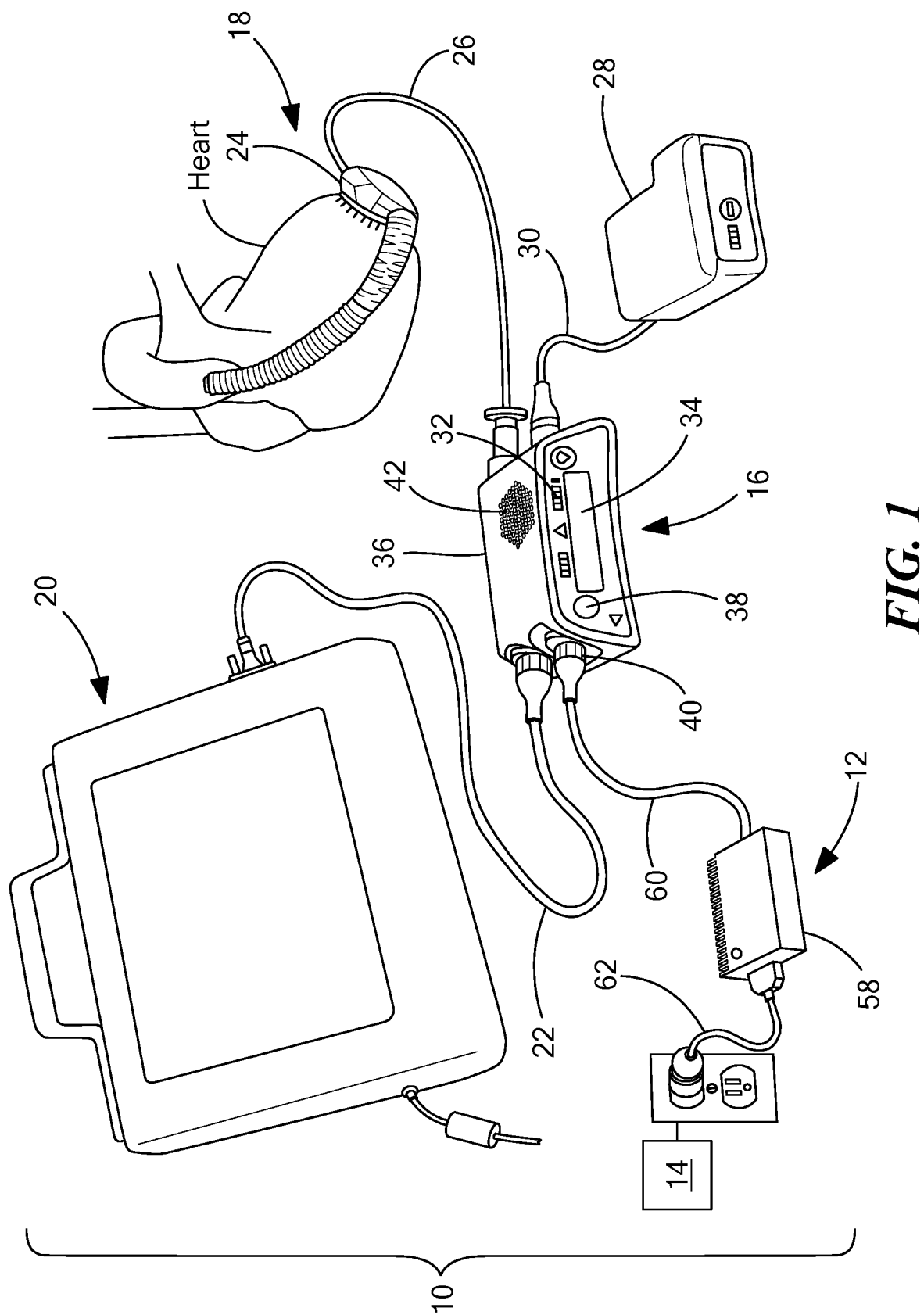
FIG. 1 shows an exemplary medical system including an intermediate power supply having a sensing and communication system, the intermediate power supply being in electrical communication with a main power source and a control system, and the control system being in electrical communication with a clinical device.

Before describing in detail exemplary embodiments, it is noted that the embodiments reside primarily in combinations of apparatus components and processing steps related to extraction of data from a clinical device and automatically analyzing completeness of that data. The system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Figure 2:
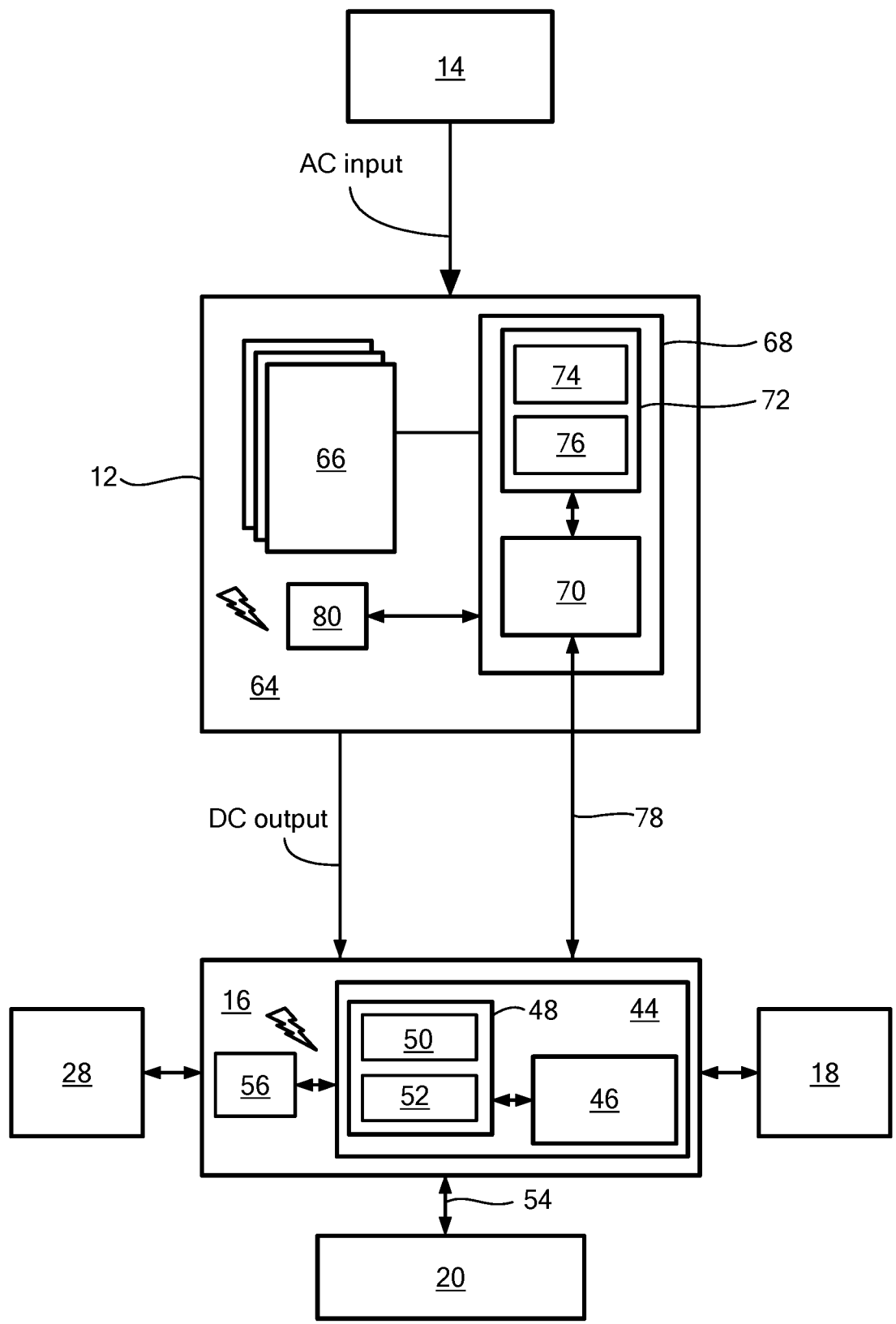
FIG. 2 shows a block diagram of the exemplary medical system of FIG. 1.

Referring now to FIGS. 1 and 2, an exemplary medical system 10 is shown. In one embodiment, the medical system 10 includes an intermediate power supply 12 in electrical communication with a main power source 14 and a control system 16, the control system 16 being in electrical communication with a clinical device 18. In some embodiments, the medical system 10 also includes a user input display 20 for communicating information to and receiving information from a user. For example, the user input display 20 may be a touch screen tablet or monitor by which the user can make menu selections, edit operating parameters of the medical system, enter user information, clear alerts and alarms, and the like. The user input display 20 also is in wired or wireless electrical communication with the control system 16 (for example, through a cable 22 as shown in FIG. 1) and is configured to receive continuous data from the control system 16 and display real-time and historical information about the clinical device 18. Although the user input display 20 is configured to both receive and communicate/display information to the user, it is referred to herein as a user input display for simplicity.

In one embodiment, the clinical device 18 is a blood pump or VAD. In the exemplary medical system 10 shown in FIG. 1, the at least a portion of the clinical device 18 is configured to be implanted within the body of a patient. In one embodiment, the clinical device 18 includes a pump 24 that is configured to be implanted within a ventricle of the patient's heart and a percutaneous driveline cable 26 that is in electrical communication with both the pump 24 and the control system 16.

In one embodiment, the medical system 10 also includes one or more rechargeable batteries 28. In the exemplary medical system 10 shown in FIG. 1, one battery 28 is in electrical communication with the control system 16 through a cable 30. Thus, power from the battery is supplied to the clinical device 18 through the control system 16. However, it will be understood that the medical system 10 may include more than one battery 28 in electrical communication with the control system 16 and clinical device 18. Further, in some embodiments, the medical system 10 may be sold as a kit that includes a plurality of batteries 28 (for example, four batteries 28) and cables 30, and a battery charger (not shown), even though fewer than all the batteries 28 in the kit may be used during operation of the medical system 10. In one embodiment, each battery 28 includes at least one charge status indicator 32. Data providing information about the charge status and/or operating condition of each battery 28 is transmitted through the cable 30 to the control system 16, and this information may be displayed to the user by a display 34 on the control system and/or the user input display 20.

In one embodiment, the control system 16 includes a housing 36 that includes one or more displays 34, charge status indicators 32 showing the charge level of at least one battery 28, one or more user input elements 38 (such as buttons, switches, knobs, touch screens, and the like), at least one cable connection port 40, and/or one or more speakers 42 for sounding to the user an audible alarm or alert. The control system 16 also includes within the housing 36 processing circuitry 44 for processing, storing, transmitting, and/or receiving data to and from other components of the medical system 10 (such as the user input display 20, the intermediate power supply 12, the at least one battery 28, and/or the clinical device 18). In one embodiment, the processing circuitry 44 includes a processor 46 and a memory 48. The memory 48 stores data 50 accessible by the processor 46, including instructions and/or protocols 52 for execution by the processor 46. In one embodiment, the control system 16 also includes a communication bus 54 for the transmission of data between the control system 16 and other components of the medical system 10 through one or more parallel and/or serial connectors. Additionally or alternatively, the communication bus 54 may be integrated with one or more cables of the medical system 10 (for example, the cable 22). One communication bus 54 is shown in FIG. 2 between the control system 16 and the user input display 20; however, it will be understood that the medical system 10 may include additional communication buses 54 between the control system 16 and other components of the medical system 10. Additionally or alternatively, the control system 16 may include within the housing 36 one or more wireless communication units 56 for the wireless communication of data to and from other components of the medical system 10. For example, the wireless communication unit(s) 56 may include components for use with wireless communication technology such as BLUETOOTH®, infrared, ZIGBEE®, near-field communication (NFC), WiFi, Medical Implant Communications Service (MICS), radiofrequency (RF), and the like.

The medical system 10 also includes an intermediate power supply 12 between the main power source 14 and the control system 16, such as an AC/DC power supply, for converting alternating current (AC) mains electricity to direct current (DC) electricity to control system 16. The intermediate power supply 12 includes a housing 58 and a cable 60 that electrically connects the intermediate power supply 12 to the control system 16. The intermediate power supply may be a "power brick" with an inline configuration and detachable AC cable 62 (for example, as shown in FIG. 1). Alternatively, the housing 58 of the intermediate power supply 12 may connect directly to the main power source 14 (for example, may plug directly into a wall outlet). In one embodiment, the intermediate power supply 12 includes within the housing 58 a transformer to reduce the voltage of the mains electricity suitable for use in powering the medical system 10 (for example, for powering the user input display 20, the control system 16, the clinical device 18, and/or for charging the battery 28), a rectifier to convert AC electricity to DC electricity, and one or more filters. In another embodiment, the intermediate power supply 12 is a switched-mode power supply (SMPS), which includes within the housing 58 a switching circuit and transformer to output DC electricity at the desired voltage. However, it will be understood that the intermediate power supply may have any suitable size and configuration.

Unlike currently known intermediate power supplies, the intermediate power supply 12 of the present Application also includes within the housing 58 a system that transforms voltage, measures and/or records one or more operating parameters of the intermediate power supply 12, processes measured and/or recorded data, and communicates data to, and optionally received data from, the control system 16. This system is referred to herein as a sensing and communication system 64. The sensing and communication system 64 measures, records, and/or processes data from one or more sensors 66 within the intermediate power supply 12 and transmits and, optionally, receives data from the control system 16. The sensing and communication system 64 also includes processing circuitry 68 for processing, storing, logging, transmitting, and/or receiving data to and from the control system 16, user input display 20, and/or the clinical device 18 (for example, as shown in FIG. 2). In one embodiment, the processing circuitry 68 includes firmware and a processor 70 and a memory 72. The memory 72 stores data 74 accessible by the processor 70, including instructions and/or protocols 76 for execution by the processor 70. The one or more sensors 66 include at least one of a piezoelectric sensor, a temperature sensor, a humidity sensor, an accelerometer, a gyroscope sensor, an impedance sensor, a voltage sensor, an etched fiber sensor or other fluid ingress sensor, a current sensor, a time sensor (for example, a timer or clock), and the like. In one embodiment, the intermediate power supply 12 includes one or more timers (time sensors) for establishing measuring intervals over which data is recorded and/or stored from the sensor(s) 66 and/or for measuring or recording a portion of, or the entirety of, the operating time of the intermediate power supply 12 (and/or the clinical device 18, control system 16, or medical system 10 as a whole). As a non-limiting example, data recorded and/or stored over one or more measuring intervals may include maximum values (such as temperature, current, voltage, etc.), minimum values (such as temperature, current, voltage, etc.), average values (such as temperature, current, voltage, etc.), and/or efficiency values or indications (such as current over time, voltage over time, etc.). The intermediate power supply 12 may also include data stored in the memory 72 with manufacturing information about the intermediate power supply 12 or other medical system 10 component (for example, test data, serial number, manufacture date), and the instructions 76 in the memory 72 may include instructions regarding one or more alerts. For example, the alert instructions may include data regarding threshold values (temperature, line input current supplied to the intermediate power supply 12, output current, line voltage, output voltage, and/or impedance), threshold rates of change, acceptable operating ranges for current, temperature, and/or voltage, a determination that fluid has entered the intermediate power supply 12, abuse event (such as impact from being dropped or hit), and the like. These alert instructions, when received by the processing circuitry 44 of the control system 16, may determine a type of alert generated by the control system 16 (for example, an audible alert or a visual alert), a duration of an alert (for example, a length of time an alert is sounded or displayed to the user and/or steps the user is required to perform to cancel the alert), and the like. Additionally, the processing circuitry 44 of the control system 16 may be configured to log alert instructions received from the intermediate power supply 12.

In one embodiment, the intermediate power supply 12 also includes a communication bus 78 for the transmission of data between the intermediate power supply 12 and other components of the medical system 10 (for example, the control system 16 and/or the user input display 20) through one or more parallel and/or serial connectors. In one embodiment, the communication bus 78 may be integrated with one or more cables of the medical system 10 (for example, the cable 60). Additionally or alternatively, the intermediate power supply 12 may include within the housing 58 one or more wireless communication units 80 for the wireless communication of data to and from other components of the medical system 10 (for example, the control system 16 and/or the user input display 20). For example, the wireless communication unit(s) 80 may include components for use with wireless communication technology such as BLUETOOTH®, infrared, ZIGBEE®, near-field communication (NFC), WiFi, MICS, RF, and the like.

Figure 3:
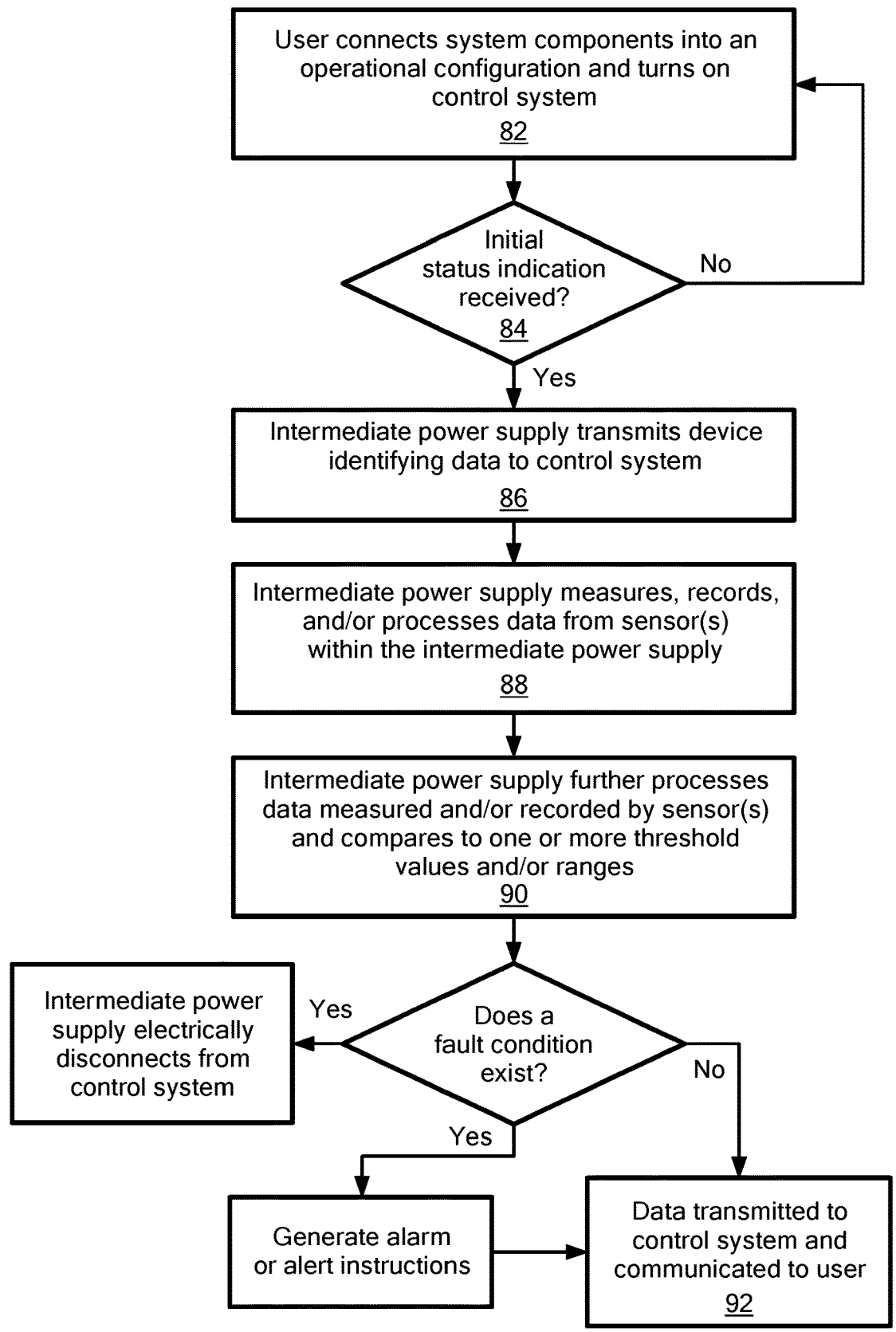
FIG. 3 shows a flow chart of an exemplary method of use of an intermediate power supply having a sensing and communication system.

Referring now to FIG. 3, an exemplary method of use of an intermediate power supply 12 with a sensing and communication system 64 is shown. In a first step 82, the user connects the components of the medical system 10 in an operational configuration. For example, the medical system 10 may be configured as shown in FIG. 1, with all cables 22, 26, 30, 60, 62 properly interconnected. In this configuration, the intermediate power supply 12 is connected to the main power source 14 (that is, the intermediate power supply 12 is plugged into an outlet and is receiving mains electricity). In this step 82, the user also turns on or activates the control system 16, user input device 20, and other components of the medical system 10.

In a second step 84, the sensing and communication system 64 transmits an initial status indication to the control system 16, which communicates to the user whether the intermediate power supply 12 is properly receiving mains electricity from the main power source 14 and is properly transmitting DC electricity to the control system 16. In one embodiment, the control system 16 includes a timer that searches for the initial status indication from the intermediate power supply 12 over a predetermined time interval. If electricity is not properly flowing through the intermediate power supply 12, and the initial status indication is not received from the intermediate power supply 12 within the predetermined time interval, the control system 16 will generate an alert to the user. For example, the control system 16 may display, through the user input display 20, a message asking the user to verify all cables and system components are properly connected and the intermediate power supply 12 is plugged into an outlet (that is, connected to the main power source 14). As another example, the control system 16, through the user input display 20, may prompt the user to identify problems with the control system 16, intermediate power supply 12, and/or other components of the medical system 10. Also, the user input display 20 may enable the user to visually and/or audibly interact with the intermediate power supply 12 in the user's native language. In one embodiment, the control system 16 and/or user input display 20 is configured to receive audible information from the user (that is, record and process a voice command or other spoken instructions or information from the user) and audibly communicate information to the user (that is, "speak" to the user) in the user's native language.

In an optional third step 86, the sensing and communication system 64 of the intermediate power supply 12 also transmits data to the control system 16 that includes information about the intermediate power supply 12 such as serial number, test data, manufacture date, and the like (referred to herein as device identifying data). In one embodiment, the control system 16 uses this data to determine whether the intermediate power supply 12 is appropriate for use with the medical system 10. If it is, the control system 16 may continue to operate normally and the method may proceed to the next step. If, on the other hand, the control unit 16 determines that the intermediate power supply 12 is not appropriate for use with the medical system 10, the control unit 16 may communicate an alert to the user through the control unit 16, user input display 20, and/or other system component.

In a fourth step 88, the sensing and communication system 64 of the intermediate power supply 12 measures, records, and/or processes data from the one or more sensors 66 within the intermediate power supply 12. As a non-limiting example, the one or more sensors 66 may include: a voltage sensor that measures and records line voltage from the main power source 14 and output voltage from the intermediate power supply 12 to the control system 16; a humidity sensor that measures and records relative humidity and/or changes in humidity; a current sensor that measures and records line current from the main power source 14 and output current from the intermediate power supply 12 to the control system 16; a temperature sensor that measures and records an operating temperature of the intermediate power supply 12; a fluid ingress sensor that detects if a fluid (for example, water, saline, or other liquid) enters the housing 58 of the intermediate power supply 12; and/or a piezoelectric sensor and/or an accelerometer that detects and quantifies an abuse event (for example, if the intermediate power supply 12 is dropped or is impacted by another object, or if gas pressure within the housing 58 increases). The portion of the data 74 in the memory 72 that is received by the processing circuitry 68 from the sensor(s) may be referred to as measurement data.

In a fifth step 90, the processing circuitry 68 further processes the data 74 that has been measured/recorded by the one or more sensors 66 and, optionally, compares the processed data to one or more threshold values or ranges to determine whether an alert instructions should be generated. An alarm may be considered a type of alert and, therefore, both are referred to herein as an alert for simplicity. The portion of the data 74 in the memory 72 that is processed from the measurement data and/or compared to the threshold value(s) may be referred to as operations data. Put another way, the processing circuitry 68 compares the measurement data received from the sensor(s), compares the measurement data to one or more threshold values or ranges to generate operations data and/or alert instructions, then transmits the operations data and/or the alert instructions to the control system 16. In one non-limiting example, temperature data may be continuously recorded by a temperature sensor and compared to a threshold operating temperature at predetermined time intervals (for example, every second or every five seconds). This comparison may be used by the processing circuitry 44 to determine whether the operating temperature of the intermediate power supply 12 has exceeded a threshold operating temperature. If the threshold temperature is exceeded, the processing circuitry 68 may then generate alert instructions. The alert instructions may include data that, when received by the processing circuitry 44 of the control system 16, instructs the control system 16 to sound an audible alert through a speaker 42 and/or generate a visual alert through the user input display 20, the display 34 on the control system 16, or other light, icon, or visual indicia. As a further non-limiting example, line voltage and/or output voltage data may be continuously recorded by a voltage sensor and compared to a threshold line voltage and/or threshold output voltage that is predetermined based on safe operating parameters of the intermediate power supply 12, the control system 16, the clinical device 18, and/or other components of the medical system 10. If the threshold line voltage and/or threshold output voltage is exceeded, the processing circuitry 68 may generate alert instructions. In addition to or instead of generating alert instructions, the intermediate power supply 12 may automatically shut down/electrically disconnect from the control system 16 (that is, terminate the output of electricity to the control system 16) if the sensing and communication system 64 determines a fault condition exits (such as fluid ingress, excessive temperature/voltage/current, or the like). In one embodiment, the intermediate power supply 12 may electrically disconnect from the control system 16 based on the alert instructions generated by the intermediate power supply 12 in response to a comparison between one or more operating parameter values to one or more threshold values.

In a sixth step 92, the sensing and communication system 64 of the intermediate power supply 12 transmits and, optionally, receives processed and/or raw data from the control system 16. In one non-limiting example, the sensing and communication system 64 transmits data to the processing circuitry 44 of the control system 16 that instructs the control system 16 to sound an audible alert, generate a visual alert, display one or more operating parameters and/or warning messages on the user input display 20, or the like. In some embodiments, the user is able to access a menu option in the user input display 20 for viewing information about the intermediate power supply 12. For example, the user may view the model and serial number of the intermediate power supply 12, verify that the intermediate power supply 12, cable 60, and/or detachable AC cable 62 are properly connected and operational (for example, are properly receiving mains electricity from the main power source 14 and outputting DC electricity having a voltage and current suitable for the medical system 10), view real-time operating parameters of the intermediate power supply 12, such as temperature, line and output voltage, line and output current, total usage of the medical system 10, occurrence of abuse events with time stamps and severity level, alarm and alert instructions, and the like. In one non-limiting example, total usage of the medical system 10 may be expressed in at least one of voltage, current, and time (for example, total operating time of the medical system 10). Based on this information, the user may take steps to remedy any identified faults (for example, may reconnect the cables 60, 62 of the intermediate power supply 12 to the housing 58, the wall outlet, and/or the control system 16, may replace the intermediate power supply 12 with a new intermediate power supply if data shows the original intermediate power supply 12 has been damaged by an abuse event, fluid ingress, or the like).

It will be understood that the steps shown in FIG. 3 may be performed in a different order, or more than one step may be performed simultaneously. For example, the sensing and communication system 64 may record data (third step 86) and transmit raw and/or processed data to the control unit 16 (fourth step 88) simultaneously.

The present disclosure provides systems, devices, and methods for sensing and communicating one or more operating parameters of system components of a medical system, such as one including a VAD. However, those skilled in the art will recognize that the same principles are applicable to other clinical devices, such as pacemakers, defibrillators, artificial hearts, or any other electronic device that may be implanted in or mounted on a patient and includes a control system that is powered by electricity from a main power source and AC/DC or intermediary power supply. Likewise, the same principles may apply to clinical devices that are fully implanted and use wireless/transcutaneous energy transfer. In one embodiment, the clinical device 18 and one or more batteries 28 are fully implanted within the patient's body, and the one or more batteries 28 are chargeable by inductive charging, which removes the requirement for the driveline cable 26.

In one embodiment, a medical system 10 comprises: a clinical device 18; a control system 16 in electrical communication with the clinical device 18; and an intermediate power supply 12 in electrical communication with the control system 16, the intermediate power supply 12 being configured to be in electrical communication with a main power source 14, the intermediate power supply 12 including a sensing and communication system 64 having: at least one sensor 66; and processing circuitry 68 in communication with the at least one sensor 66.

In one aspect of the embodiment, the control system 16 includes processing circuitry 44, the processing circuitry 68 of the intermediate power 12 supply being configured to transmit data 74 to and receive data 74 from the processing circuitry 44 of the control system 16.

In one aspect of the embodiment, the at least one sensor 66 includes at least one of: a piezoelectric sensor; a temperature sensor; a humidity sensor; an accelerometer; an impedance sensor; a voltage sensor; a fluid ingress sensor; a current sensor; and a time sensor.

In one aspect of the embodiment, the medical system 10 further comprises a user input display 20 in electrical communication with the control system 16.

In one aspect of the embodiment, the user input display 20 is configured to receive data 74 from the control system 16 and to display information to a user, the information being based on the received data 74.

In one aspect of the embodiment, the user input display 20 is further configured to receive audible information from a user and audibly communicate information to the user in the user's native language.

In one aspect of the embodiment, the information includes at least one of: a line voltage of electricity received by the intermediate power supply from the main power source; an output voltage of electricity transmitted from the intermediate power supply to the control system; a line current of electricity received by the intermediate power supply from the main power source; an output current of electricity transmitted from the intermediate power supply to the control system; an operating temperature of the intermediate power supply; and a total usage of the medical system, the total usage being expressed in at least one of voltage, current, and time.

In one aspect of the embodiment, the processing circuitry 68 of the intermediate power supply 12 is configured to: record at least one operating parameter of the intermediate power supply 12; compare the at least one operating parameter to a threshold value; and generate alert instructions based on the comparison.

In one aspect of the embodiment, the control system 16 is configured to receive the alert instructions from the intermediate power supply 12, to log alert instructions, and to generate at least one alert based on the alert instructions, the at least one alert being at least one of: an audible alert; and a visual alert.

In one aspect of the embodiment, the user input display 20 is configured to display the visual alert.

In one aspect of the embodiment, the processing circuitry 68 of the intermediate power supply 12 is further configured to automatically electrically disconnect from the control system 16 based on the alert instructions.

In one aspect of the embodiment, the sensing and communication system 64 further has a wireless communication unit 80 configured to wirelessly transmit and receive data 74 from the control system 16.

In one aspect of the embodiment, the sensing and communication system 64 further has a communication bus 78 configured to transmit and receive data 74 from the control system 16.

In one aspect of the embodiment, the clinical device 18 is a ventricular assist device.

In one embodiment, an intermediate power supply 12 is configured to be connected between a main power source 14 and a control system 16 of a medical system 10. In this embodiment, the intermediate power supply 12 comprises: at least one sensor 66, the at least one sensor being configured to record data 74 relating to at least one operating parameter of the intermediate power supply 12; and processing circuitry 68 in communication with the at least one sensor 66, the processing circuitry 68 being configured to receive the data 74 from the at least one sensor 66 and to compare the data to at least one threshold value.

In one aspect of the embodiment, the intermediate power supply 12 is configured to receive alternating current electricity from a main power source 14 and to transmit direct current electricity.

In one aspect of the embodiment, the intermediate power supply 12 is configured to be in electrical communication with, and transmit direct current electricity to, a control system 16 of a medical system 10.

In one aspect of the embodiment, the intermediate power supply 12 is configured to automatically electrically disconnect from the control system 16 based on the comparison.

In one aspect of the embodiment, the intermediate power supply 12 is configured to generate alert instructions based on the comparison.

In one aspect of the embodiment, the at least one sensor 66 includes at least one of: a piezoelectric sensor; a temperature sensor; a humidity sensor; an accelerometer; an impedance sensor; a voltage sensor; a fluid ingress sensor; a current sensor; and a time sensor.

In one embodiment, an intermediate power supply 12 for use with a medical system 10 is configured to receive alternating current electricity from a main power source 14 and to transmit direct current electricity to a control system 16 of the medical system 10. In this embodiment, the intermediate power 12 supply comprises: at least one sensor 66; and processing circuitry 68 in communication with the at least one sensor 66, the processing circuitry 68 including a memory 72 and a processor 70, the memory 72 in communication with the processor 70, the memory 72 having instructions that, when executed by the processor 70, configure the processor 70 to: receive measurement data from the at least one sensor 66; compare the measurement data to a threshold value to generate at least one of operations data and alert instructions; and transmit the at least one of operations data and alert instructions to a control system 16 of a medical system 10.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system comprising:
an implantable blood pump;
a control system in electrical communication with the implantable blood pump; and
an intermediate power supply in electrical communication with the control system, the intermediate power supply being configured to be in electrical communication with a main power source, the intermediate power supply including a sensing and communication system having:
at least one sensor; and
processing circuitry in communication with the at least one sensor.

2. The medical system of claim 1, wherein the control system includes processing circuitry, the processing circuitry of the intermediate power supply being configured to transmit data to and receive data from the processing circuitry of the control system.

3. The medical system of claim 2, wherein the at least one sensor includes at least one of a piezoelectric sensor, a temperature sensor, a humidity sensor, an accelerometer, an impedance sensor, a voltage sensor, a fluid ingress sensor, a current sensor, and a time sensor.

4. The medical system of claim 2, further comprising:
a user input display in electrical communication with the control system.

5. The medical system of claim 4, wherein the user input display is configured to receive data from the control system and to display information to a user, the information being based on the received data.

6. The medical system of claim 5, wherein the user input display is further configured to receive audible information from a user and audibly communicate information to the user in the user's native language.

7. The medical system of claim 5, wherein the information includes at least one of:
a line voltage of electricity received by the intermediate power supply from the main power source;
an output voltage of electricity transmitted from the intermediate power supply to the control system;
a line current of electricity received by the intermediate power supply from the main power source;
an output current of electricity transmitted from the intermediate power supply to the control system;
an operating temperature of the intermediate power supply; and
a total usage of the medical system, the total usage being expressed in at least one of voltage, current, and time.

8. The medical system of claim 5, wherein the processing circuitry of the intermediate power supply is configured to:
record at least one operating parameter of the intermediate power supply;
compare the at least one operating parameter to a threshold value; and
generate alert instructions based on the comparison.

9. The medical system of claim 8, wherein the control system is configured to receive the alert instructions from the intermediate power supply, to log alert instructions, and to generate at least one alert based on the alert instructions, the at least one alert being at least one of:
an audible alert; and
a visual alert.

10. The medical system of claim 9, wherein the user input display is configured to display the visual alert.

11. The medical system of claim 8, wherein the processing circuitry of the intermediate power supply is further configured to automatically electrically disconnect from the control system based on the alert instructions.

12. The medical system of claim 1, wherein the sensing and communication system further has a wireless communication unit configured to wirelessly transmit and receive data from the control system.

13. The medical system of claim 1, wherein the sensing and communication system further has a communication bus configured to transmit and receive data from the control system.

14. An intermediate power supply configured to be connected between a main power source and a control system of a medical system, the intermediate power supply comprising:
at least one voltage or current one sensor, the at least one voltage or current sensor being configured to record data relating to at least one operating parameter of the intermediate power supply; and
processing circuitry in communication with the at least one voltage or current sensor, the processing circuitry being configured to receive the data from the at least one voltage or current sensor and to compare the data to at least one threshold value.

15. The intermediate power supply of claim 14, wherein the intermediate power supply is configured to receive alternating current electricity from a main power source and to transmit direct current electricity.

16. The intermediate power supply of claim 15, wherein the intermediate power supply is configured to be in electrical communication with, and transmit direct current electricity to, a control system of a medical system.

17. The intermediate power supply of claim 16, wherein the intermediate power supply is configured to automatically electrically disconnect from the control system based on the comparison.

18. The intermediate power supply of claim 14, wherein the intermediate power supply is configured to generate alert instructions based on the comparison.

19. An intermediate power supply for use with a medical system, the intermediate power supply being configured to receive alternating current electricity from a main power source and to transmit direct current electricity to a control system of the medical system, the intermediate power supply comprising:
at least one voltage or current sensor; and
processing circuitry in communication with the at least one voltage or current sensor, the processing circuitry including a memory and a processor, the memory in communication with the processor, the memory having instructions that, when executed by the processor, configure the processor to:
receive measurement data from the at least one voltage or current sensor;
compare the measurement data to a threshold value to generate at least one of operations data and alert instructions; and
transmit the at least one of operations data and alert instructions to a control system of a medical system.

* * * * *